United States Patent
Powell

[11] Patent Number: 5,876,459
[45] Date of Patent: Mar. 2, 1999

[54] ADJUSTABLE MODULAR ORTHOPEDIC IMPLANT

[76] Inventor: Douglas Hunter Powell, 44910 S. El Macero Dr., El Macero, Calif. 95618

[21] Appl. No.: 706,406

[22] Filed: Aug. 30, 1996

[51] Int. Cl.[6] .................................. A61F 2/30; A61F 2/36
[52] U.S. Cl. ................................................ 623/18; 623/23
[58] Field of Search ................................... 623/16, 18, 20, 623/22, 23

[56] References Cited

U.S. PATENT DOCUMENTS

| | | | |
|---|---|---|---|
| 3,846,846 | 11/1974 | Fischer | 623/23 |
| 4,502,160 | 3/1985 | Moore et al. | 623/18 |
| 4,520,511 | 6/1985 | Gianezio et al. | 623/23 |
| 4,995,883 | 2/1991 | Demane et al. | 623/23 |
| 5,002,578 | 3/1991 | Luman | 623/23 |
| 5,035,712 | 7/1991 | Hoffman | 623/23 X |
| 5,507,817 | 4/1996 | Craig et al. | 623/23 X |
| 5,507,830 | 4/1996 | DeMane et al. | 623/23 |
| 5,569,263 | 10/1996 | Hein | 623/23 X |
| 5,653,765 | 8/1997 | McTighe et al. | 623/18 X |
| 5,658,349 | 8/1997 | Brooks et al. | 623/18 X |

FOREIGN PATENT DOCUMENTS

WO 91/11155  8/1991  WIPO ..................................... 623/23

*Primary Examiner*—Mary Beth Jones
*Attorney, Agent, or Firm*—Hall & Kerr

[57] ABSTRACT

An implantable modular orthopedic prosthesis, preferably for hip or knee arthroplasty, is disclosed which consists of three components. A first component has an elongated stem with a free end, configured to be situated within the intramedullary canal of a patient's bone, and an opposite end having an articulating portion such as a Morse-tapered member. A second component has another articulating portion which can also be a corresponding Morse-tapered member that is matingly engageable with the articulating portion of the first component. A third component has a body with a linearly-extruded channel through which the articulating portions are adjustably received, wherein at least one of the components is radially-expansible to pressure lock against an internal surface of the channel in a selected position and arrest the first, second and third components together as the articulating portions are fully engaged with one another. The present modular orthopedic implant functions as a unitary biomechanical structure and is easy to use, as it is interoperatively adjustable to fit minute variations in a patient's given anatomy, while minimizing the inventory of component sizes needed on hand during surgery.

26 Claims, 9 Drawing Sheets

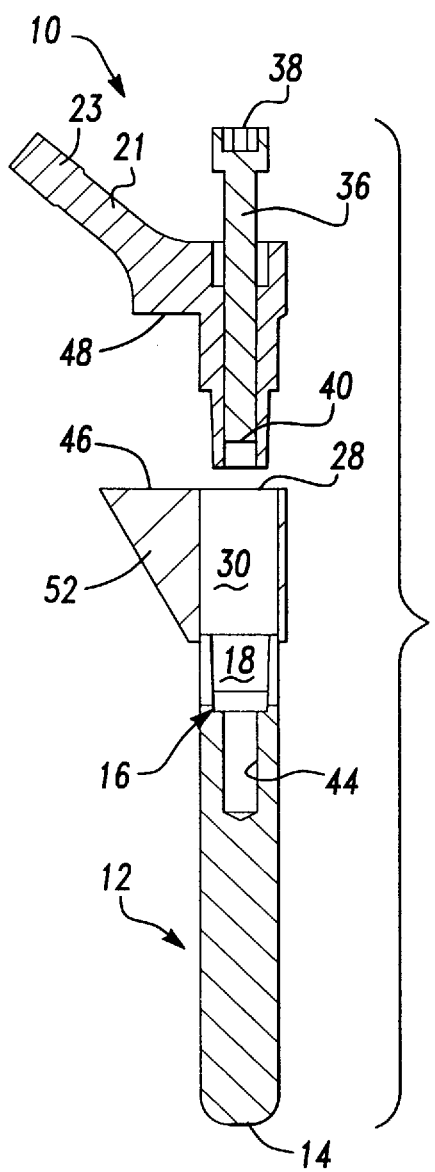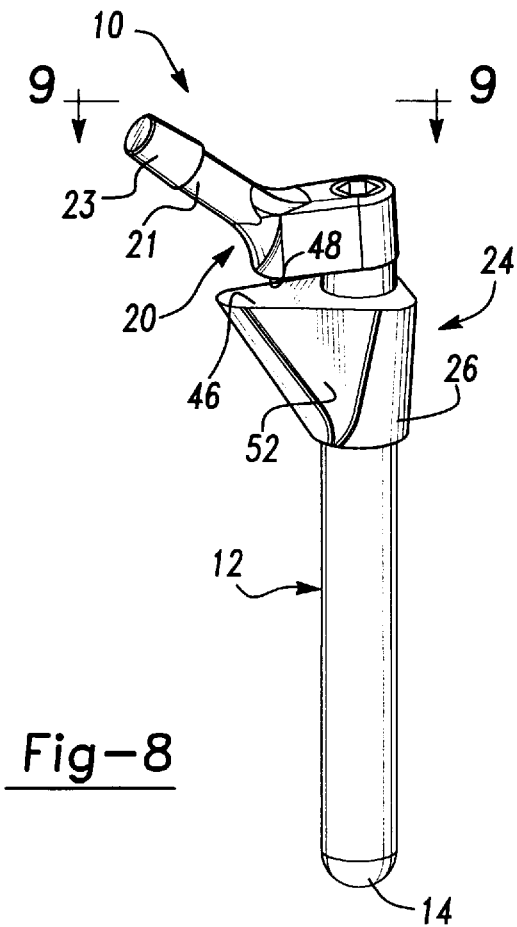
Fig-7
Fig-8

ADJUSTABLE MODULAR ORTHOPEDIC IMPLANT

BACKGROUND OF THE INVENTION

1. Field of the Invention

This invention relates generally to modular implantable orthopedic prostheses, and particularly those which are adjustable in size to fit a given patient's needs.

2. Description of the Prior Art

Various prostheses have heretofore been designed to replace one or both components of a ball and socket hip joint. Generally the ball portion is connected to an arm composed of a neck and a stem or shaft which stem or shaft is embedded in the intramedullary canal of the proximal femur for hip reconstruction. Such prostheses are often formed with an integral stem and neck portion. Often a removable ball or head element is positioned on the proximal end of the neck. See, for example, U.S. Pat. Nos. 4,012,795 or 4,459,708.

Recently the use of modular structures together from a number of replaceable parts available in a variety of sizes have been used. With such prostheses it is possible to replace either the head portion or trochanteral portion of the prostheses, or both, without removal of the stem from the bone cavity. U.S. Pat. Nos. 4,608,055, 4,676,979 and 4,693,724 are all illustrative of such approaches. The latter patent also discloses the possibility that the angle at which the neck protrudes from the proximal end of the femur (referred to in said patent as "anteversion") may be adjusted without removal of the stem by pivoting the neck on the end of the implanted stem. These prior art devices, however, failed to provide a means for varying the angle between the axis of the trochanteral module and the axis of the stem so that the actual angulation (sometimes referred to as anteversion) or slope of the proximal end of the femur may be duplicated by adjustment of said angle. U.S. Pat. Nos. 5,002,581 and 5,201,882 to Paxson, et al. filled such a need, by providing a modular device and instrumentation for implanting such device with the proper anteversion to match that of a patient's anatomy. The components of Paxson's device are secured together using complementary standard Morse-tapered connections.

Other modular hip prostheses have been proposed, which are said to address various objects of design and use, among these the achievement of a "custom fit", For example, U.S. Pat. No. 4,995,883 to Demane, et al discusses using transitional sections of variable length between the the several components of the device, secured togteher via combinations of a locking screw and Morse tapered fittings. U.S. Pat. No. 5,002,578 to Luman discloses a modular hip having a neck inserted via a shouldered member to a unitary trochanteral/stem component, with a locking screw running through its shoulder into the trochateral/stem component to secure the two components together. U.S. Pat. Nos. 5,080,685, 5,181,928, 5,286,260 and 5,370,706, all to Bolesky, each provide a modular prosthesis kit, capable of interoperative assembly by the surgeon, who chooses the proper size of components prior to implantation. U.S. Pat. No. 5,108,452 to Fallin shows a modular hip having extension sleeves to adjust the length between the ball and neck, as well as additional pads to increase the cross-sectional shape of the prosthesis body. U.S. Pat. No. 4,878,917 to Kranz et al. discloses a modular hip prosthesis having a stem with a distal tip that is radially expandable to anchor the stem against the medullary canal wall.

U.S. Pat. No. 4,846,839 to Noiles discloses a modular prosthesis design, alternatively adaptable to either total hip or knee arthroplasty, which presents a stepped contour interface with the patient's bone. The components of this design are connected via conventional Morse tapers. A further type of device used for the fixation of modular prosthesis components is sold by H. D. Holmes under the registered trademark Spiralock®, consisting of a clamping screw which fastens a standard Morse taper connection together, e. g., connecting either the tibial tray or femoral component of a total knee joint to its respective stem. A further example of the use of such locking screws in a modular hip prosthesis is found in U.S. Pat. No. 5,397,360 to Cohen.

U.S. Pat. No. 5,405,398 to Buford, III et al. discloses a knee prosthesis with a femoral component having a pin including a split ring which expands to keep the pin in place. U.S. Pat. Nos. 5,531,792 to Huene and 4,011,602 to Rybicki, et al. each show bone fixation plugs having radially expanding members to apply compressive forces against the surrounding bone and promote ingrowth of the tissue into the member. Neither of these contemplate an improved mechanism for connecting the components of modular orthopedic implants of the type used in large or small total joint arthroplasty.

The modular knee and hip joint prostheses, described above, address the need for either or both the ball component or trochanteral module component to be removed if replacement becomes necessary, without extraction of the stem from the bone canal. Different size balls or trochanteral components could also be substituted should the surgeon decide that such revision is necessary after a period of time. These conventional devices also contemplate selecting from a variety of sizes of their components, in order to match the anatomy of a given patient as closely as possible within the inherent variability of the assembly.

However, the modular systems, notwithstanding the variability offered in their assemblage of specifically sized components, fail to provide an infinite variability within a given size range while creating a biomechanical assembly of enhanced strength. That is, the prior assemblies introduce torsional stresses at the junctures of their components which do not necessarily reflect a unitary construction. Moreover, a wide array of sizes must be kept in stock during surgery to match a patient's anatomy.

Therefore there is a need for a prosthesis which relies upon an enhanced means of connecting its components together, while further providing infinite adjustability within a given size range, while forming an assembly which biomechanically functions as an integral structure.

SUMMARY OF INVENTION AND ADVANTAGES

According to the present invention, there is provided an implantable modular orthopedic prosthesis which consists of three components. A first component has an elongated stem with a free end, configured to be situated within the intramedullary canal of a patient's bone, and an opposite end having an articulating portion. A second component has another articulating portion which is matingly engageable with the articulating portion of the first component. A third component has a body with a linearly-extruded channel through which the articulating portions are adjustably received, wherein at least one of the components is radially-expansible to pressure lock against an internal surface of the channel in a selected position and arrest the first, second and third components together as the articulating portions are fully engaged with one another.

In a preferred embodiment of the invention, the prosthesis is a modular hip, while in another preferred embodiment it is a modular knee, particularly, a tibial prosthesis.

In a further preferred embodiment of the invention, the articulating portions are complementary Morse-tapered connectors.

In yet another preferred embodiment of the invention, a tensioning member urges the articulating portions together, causing the radially-expanding component to pressure-lock against the internal surface of the channel and affix the three components together. Moreover, it is further preferred that the radial-expansion take the form of a split collet mechanism.

An advantage of the present invention is an improved mechanism for interlocking the components of a modular orthopedic prosthesis which, following implantation, functions as a unitary biomechanical structure.

Another advantage of the present invention is a prosthetic system which is easy to use and interoperatively adjustable to fit minute variations in a patient's given anatomy, while minimizing the inventory of component sizes needed on hand during surgery.

BRIEF DESCRIPTION OF THE DRAWINGS

Further objects and advantages of the invention will become apparent to one skilled in the art by resort to the following Drawings, taken in conjunction with the accompanying Detailed Description, with the reference numerals given in the text corresponding to similarly numbered structures in the Drawings, wherein:

FIG. 7 is a longitudinal sectional view of the prosthesis of FIG. 5, taken along the lines 7—7 of FIG. 6;

FIG. 8 is a perspective view of the hip prosthesis of FIG. 1, shown fully assembled with the stem component in its minimally extended position;

DETAILED DESCRIPTION

Figure 1:
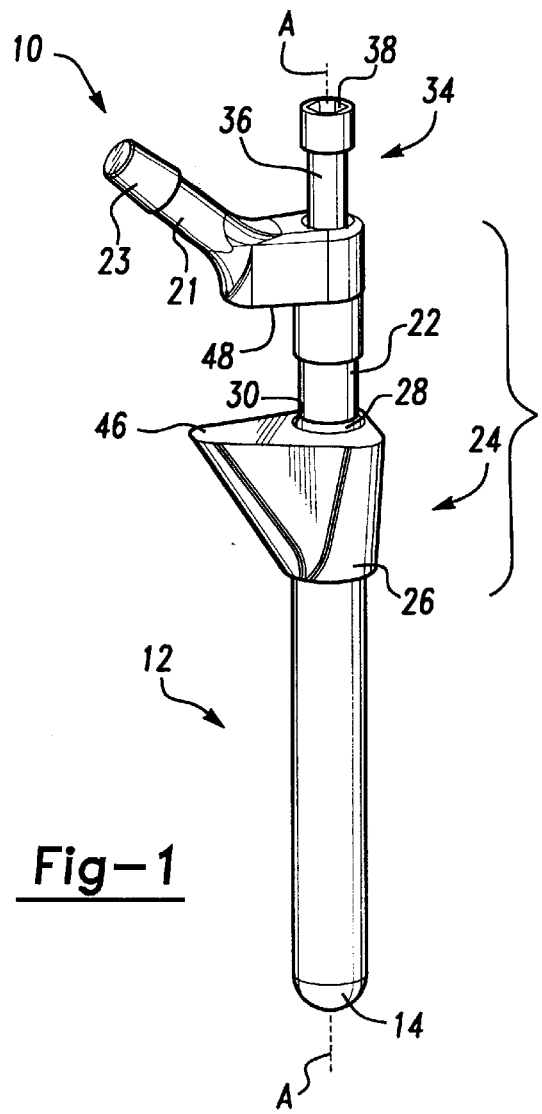
FIG. 1 is an exploded perspective view of the components of the invention embodied in a preferred modular hip prosthesis, with the components positioned for maximum stem extension.
Figure 2:
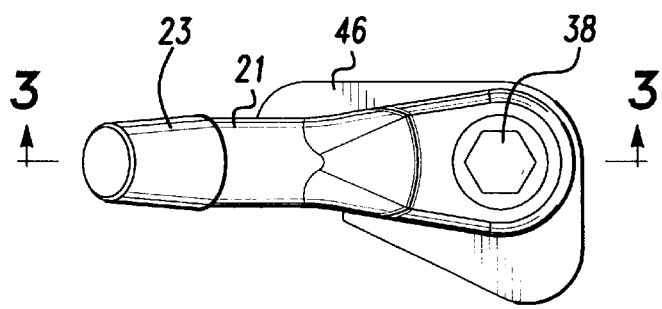
FIG. 2 is an external top view of the prosthesis of FIG. 1.
Figure 3:
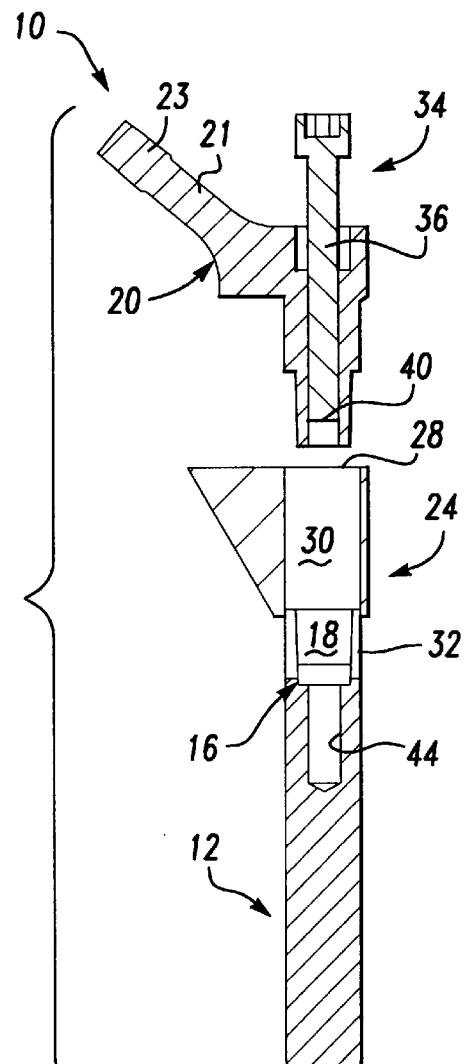
FIG. 3 is a longitudinal sectional view of the prosthesis of FIG. 2, taken along the lines 3—3.
Figure 12:
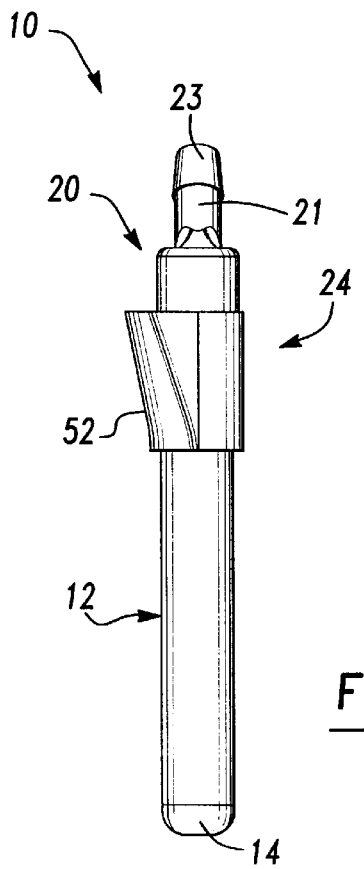
FIG. 12 is a side view of the preferred hip prosthesis of the invention, shown in an assembled state with the stem in its maximally-extended position and the trochanteric module rotated to an alternative conformation.

Referring to one or more of the preferred embodiments of the present invention, as depicted in FIGS. 1–18, there is provided an implantable modular orthopedic prosthesis, in this case a hip prosthesis, generally shown at 10, which is comprised of multiple components. A first component is an elongated stem, generally shown at 12, with a free distal end 14, configured to be situated within the intramedullary canal of a patient's bone (not shown), and an opposite end, generally indicated at 16, having an articulating portion, preferably a Morse-tapered connecting member, such as the frusto-conical bore 18. A second component is a neck, generally shown at 20, which has another articulating portion, preferably a complementary Morse-tapered connector such as the tapered post 22, which is matingly engageable with the tapered bore 18 of the stem 12. A third component is a trochanteric module, generally indicated at 24 having a contoured body 26 adapted for implantation into the resected proximal femur of a patient. A linearly-extruded channel 28 is formed through the module 24, along an axis A (FIG. 1) generally coincident with the longitudinal axis of the stem 12, with an internal surface 30. The articulating portions 18,22 are adjustably received within the channel 28, such that the module 24 can be axially moved along axis A relative to stem 12 and neck 20 to adjust the distance between the module and the neck and stem, respectively. At least one of the components is radially-expansible, preferably by means of the expanding collet mechanism 32 to pressure lock against the internal surface 30 of the channel 28 in a selected position and arrest the first (stem 12), second (neck 20) and third (module 24) components together as the articulating portions, i.e., tapered bore 18 and post 22, are fully engaged with one another. Although the tapered bore 18 and collet 32 are shown in FIG. 12 as being located on the stem 12, the location of these elements may be reversed so that they are on the neck, as will be described hereinafter with reference to FIGS. 13–18.

Referring again to FIGS. 1–18, the hip prosthesis 10 further comprises a tensioning member, generally indicated at 34, operatively connecting the stem 12 and neck 20, to urge the articulating Morse-tapered bore 18 and post 22 together and affix all three components 12, 20, 24 of the prosthesis 10 together in a desired relative conformation.

The tensioning member preferably consists of a locking bolt 34 having an elongated shaft 36 with a driven end 38 and a threaded end 40 which passes distally through an opening 42 formed in the neck 20, thence through the tapered post 18 and bore 22 to threadedly engage a tapped aperture 44 in the stem 12. Although not specifically described, the bolt 34 could alternatively be passed through an opening optionally formed in the distal end 14 of the stem 12 (not shown) and continuing proximally to engage a threaded aperture in the neck (not shown), as will be appreciated by those skilled in the art.

The linearly extruded channel 28 preferably has a circular cross section, e.g., a cylindrical bore, allowing infinitely variable rotational adjustment of the stem 12 and neck 20 relative to one another, and allowing proximal-distal adjustment of these components within the channel 28.

It will be appreciated by those skilled in the art that the channel 28 may alternatively have a polygonal cross section or a star shape (not shown) while the articulating portions could have corresponding shapes which would be respectively indexable relative to the channel in a finite selection of rotational alignments, rather than the infinite rotational adjustability afforded by the Morse-tapered connection described herein. Having a square shaped channel (not shown), for example, would allow for 4 orthogonal relative rotations of the neck 20 and stem 12, while the multi-point star shape would allow for multiple rotations of the neck and stem. The linearly extruded cut of the channel 28 also allows for the independent insertion, rotation and removal of the stem 12 without removing the anatomically press fit trochanteric module 24, once implanted. Though inserting the stem 12 from the proximal end of the neck has its advantages, inserting the stem from the distal direction proximally into the neck, prior to insertion into the femoral bone allows for greater mechanical stability and variable design flexibility.

The body 26 of trochanteric module 24 has a proximal shoulder 46 which abuts a stop 48 formed on the neck 20, limiting the range of axially adjustable telescoping movement of the surrounding trochanteric module 24 relative to the neck and stem 12, prior to full engagement of the articulating bore 18 and post 22 by tightening of the bolt 34. Module 24 has a rounded triangular cross section, adjacent the proximal shoulder 46, the area of which reduces distally, shown, e. g., in FIGS. 10–11. The neck 20 is equipped with an integral, angulated member 21 with a further Morse-tapered post 23 for attachment of a conventional ball (not shown).

Figure 4:
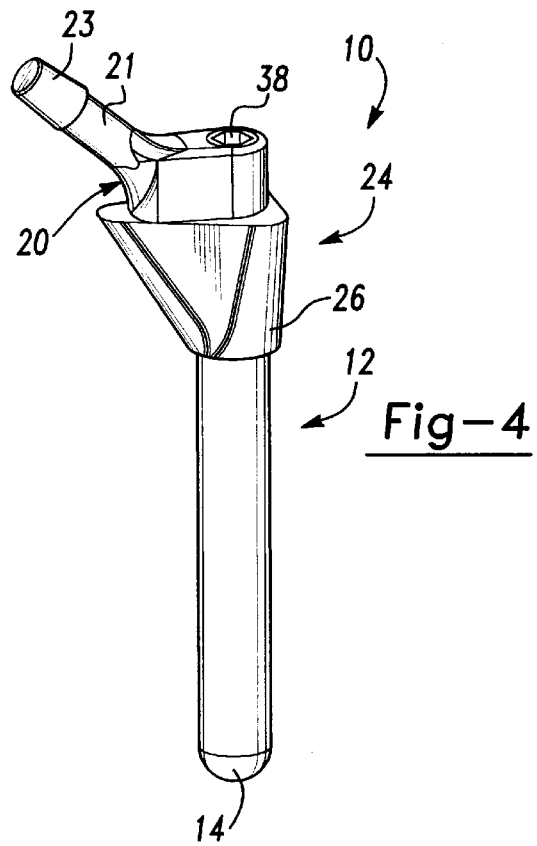
FIG. 4 is a perspective view of the hip prosthesis of FIG. 1, shown fully assembled with the stem component in its fully extended position.
Figure 5:
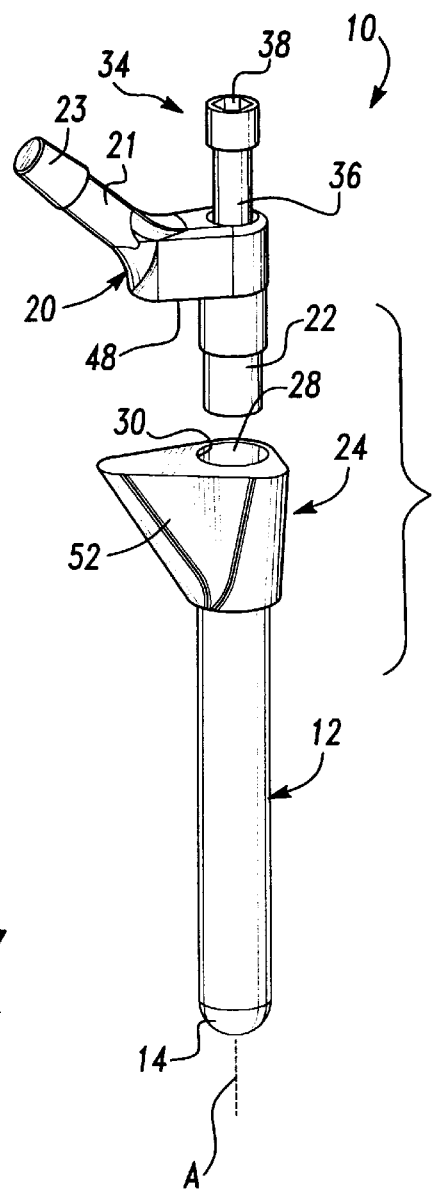
FIG. 5 is an exploded perspective view of the components of the invention embodied in a preferred modular hip prosthesis, with the components positioned for minimal stem extension.
Figure 6:
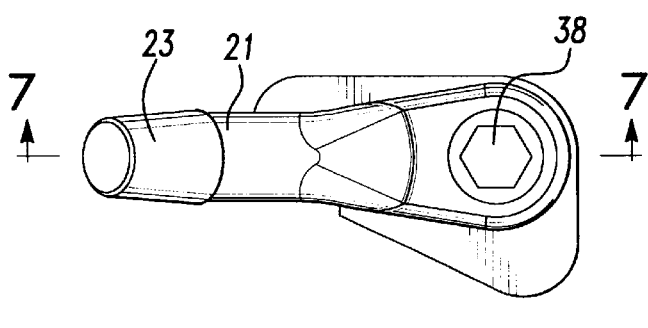
FIG. 6 is an external top view of the prosthesis of FIG. 5.

In FIG. 4, the prosthesis 10 is shown with the stem 12 in its maximally extended position, that is, the shoulder 46 abuts the stop 48 with the components 12, 20, 24 affixed together. For aesthetic purposes, the collet 32 is fully constrained within the channel 28, as shown in FIG. 4 and also in FIG. 5 where the collet 32 is actuated within channel 28 to pressure-lock against internal surface 30 in a selected location such that the shoulder 46 is axially spaced from the distal stop 48. Thus, a patient can be fitted with a fixed size of prosthetic components, then the sized components adapted to either increase (FIG. 4) or decrease (FIG. 5) the effective length of the stem 12, depending upon the patients anatomy, without resort to a more complex assortment of intermediate sizes of trial implants and prosthetic components.

Figure 9:
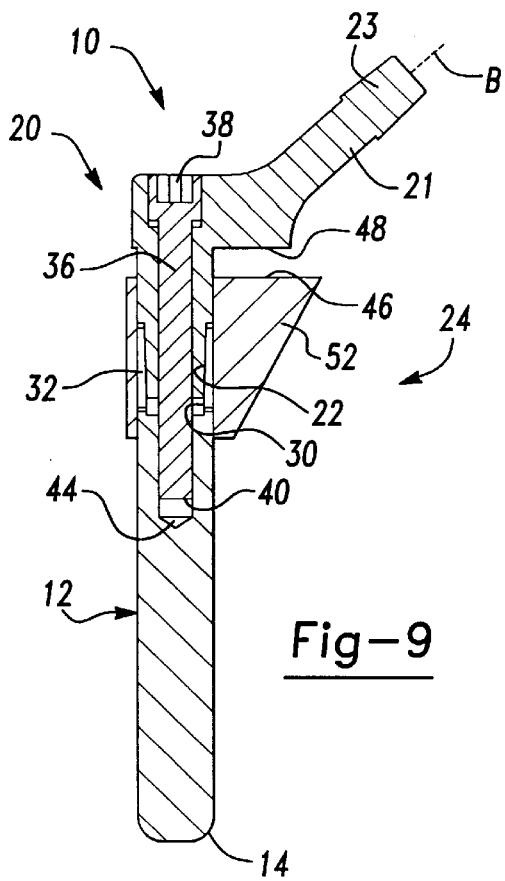
FIG. 9 is a longitudinal sectional view of the prosthesis of FIG. 8, taken along the lines 9—9.
Figure 10:
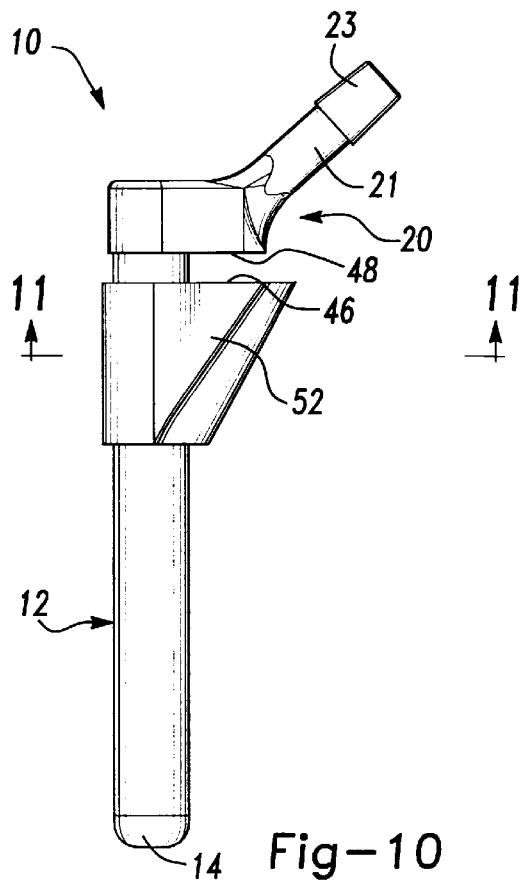
FIG. 10 is a side view of the hip prosthesis of FIG. 1, shown fully assembled with the stem component in its minimally extended position.
Figure 11:
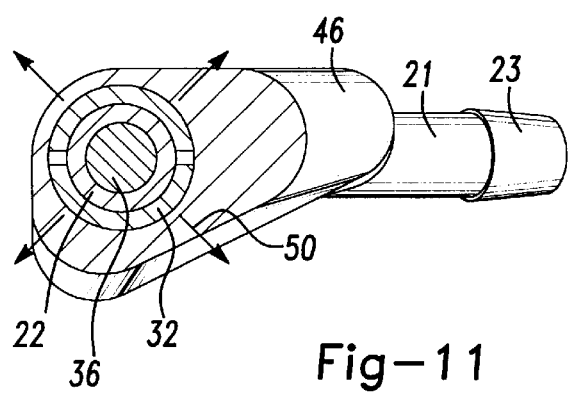
FIG. 11 is a transverse sectional view of the hip prosthesis of FIG. 8, taken along the lines 11—11, showing the preferred expanded collet mechanism of the invention located on the stem.
Figure 13:
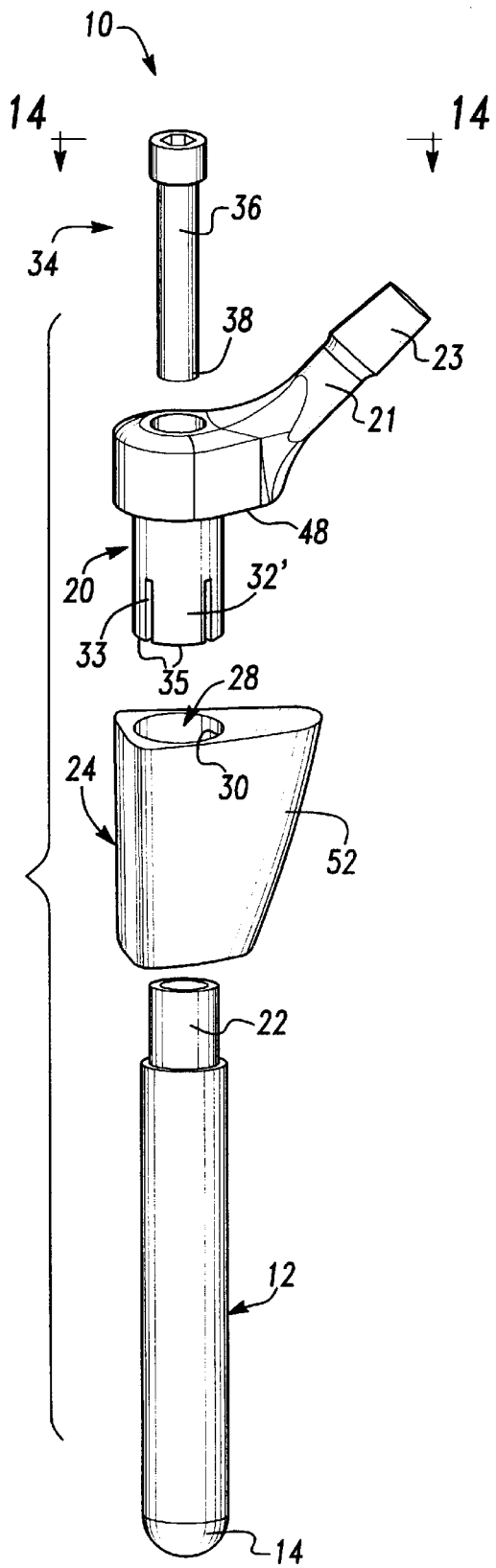
FIG. 13 is an exploded perspective view of the components of the invention embodied in a preferred modular hip prosthesis, with the expanding collet mechanism located on the neck.
Figure 14:
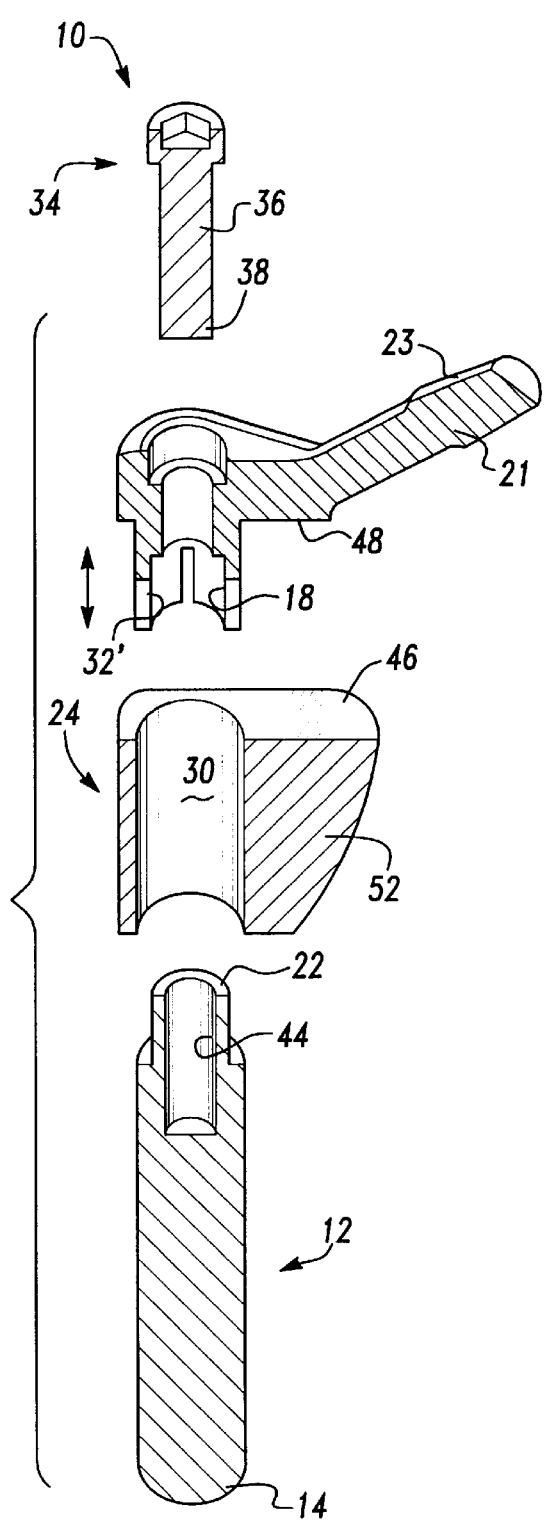
FIG. 14 is a longitudinal sectional exploded view of the prosthesis of FIG. 13, taken along the lines 14—14.
Figure 15:
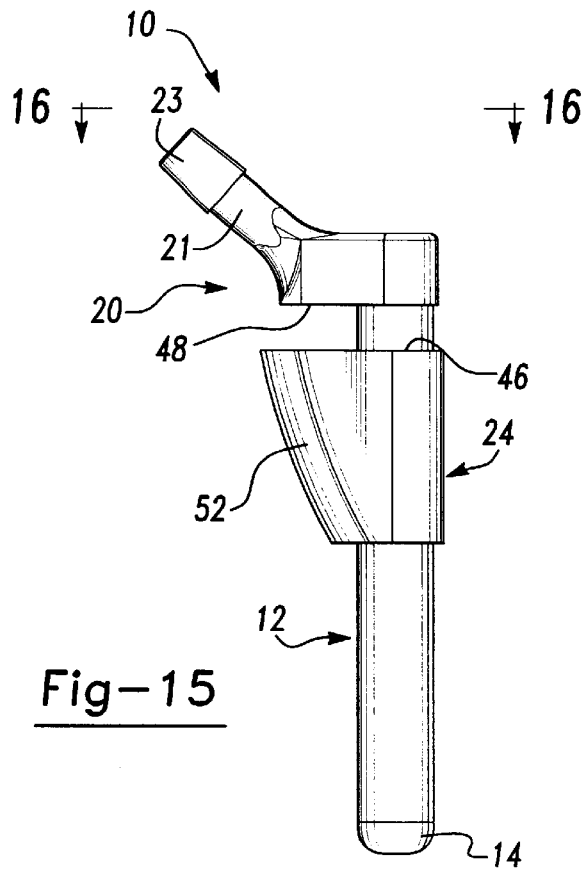
FIG. 15 is a side of the hip prosthesis of FIG. 13, shown fully assembled with the stem component in its maximally extended position.
Figure 16:
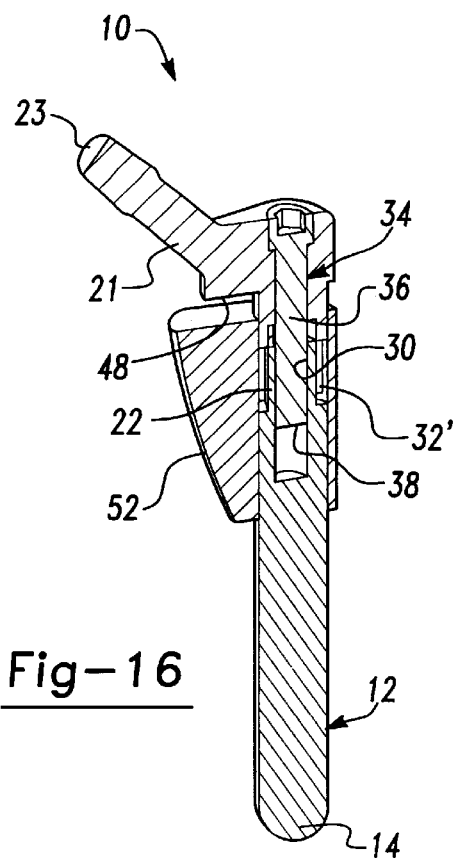
FIG. 16 is a top plan sectional view of the prosthesis of FIG. 15, taken along the lines 16—16.
Figure 17:
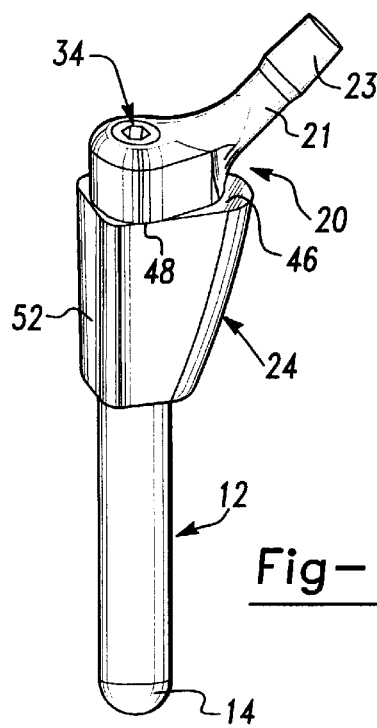
FIG. 17 is a perspective view of the hip prosthesis of FIG. 13, shown fully assembled with the stem component in its maximally extended position.
Figure 18:
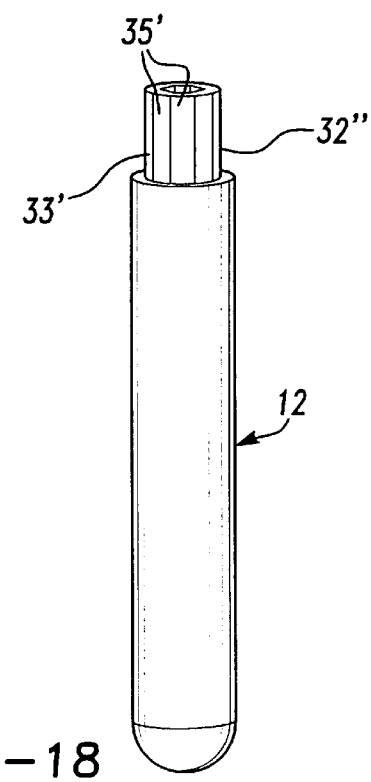
FIG. 18 is a longitudinal sectional view of the prosthesis of FIG. 17, taken along the lines 18—18.
Figure 19:
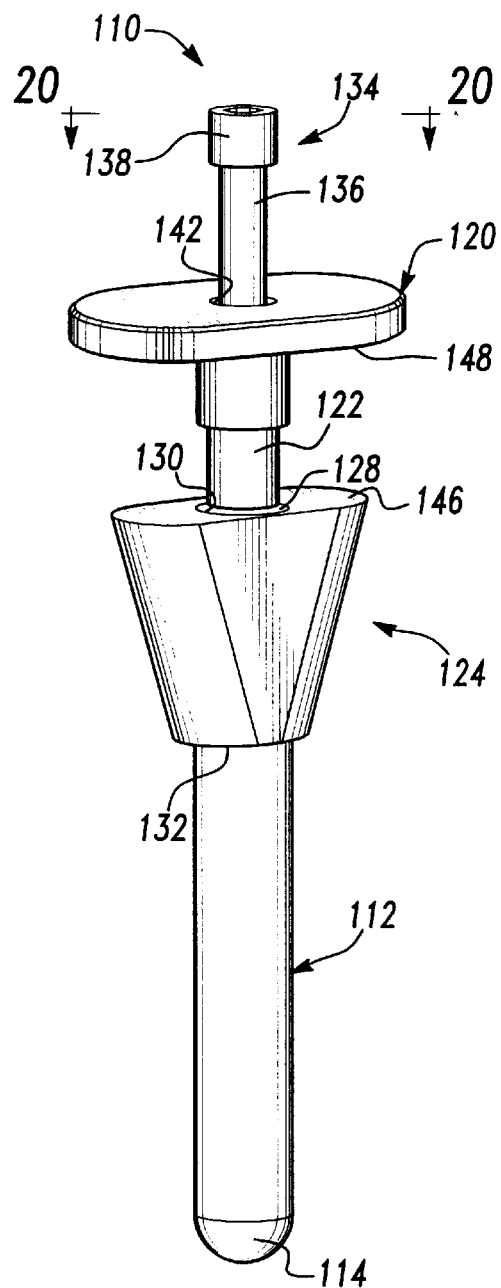
FIG. 19 is an exploded perspective view of the components of the invention embodied in a preferred modular tibial prosthesis, with the expanding collet mechanism located on the stem.
Figure 20:
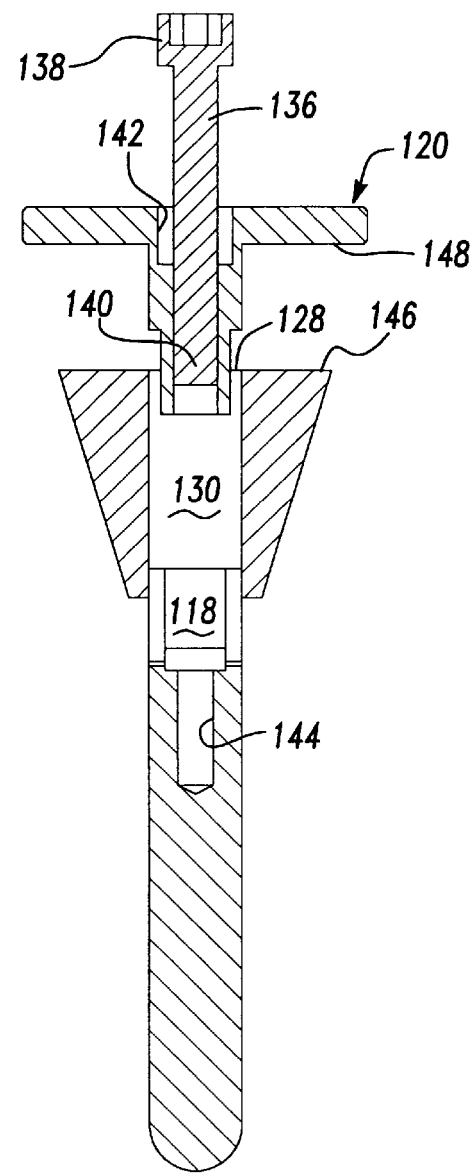
FIG. 20 is a longitudinal sectional view of the tibial prosthesis of FIG. 19, taken along the lines 20—20.
Figure 21:
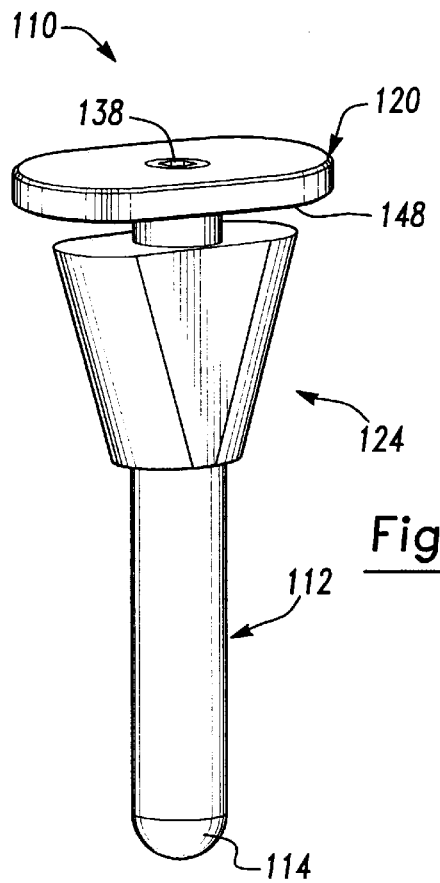
FIG. 21 is a perspective view of the tibial prosthesis of FIG. 19, shown fully assembled with the stem component in its minimally extended position.
Figure 22:
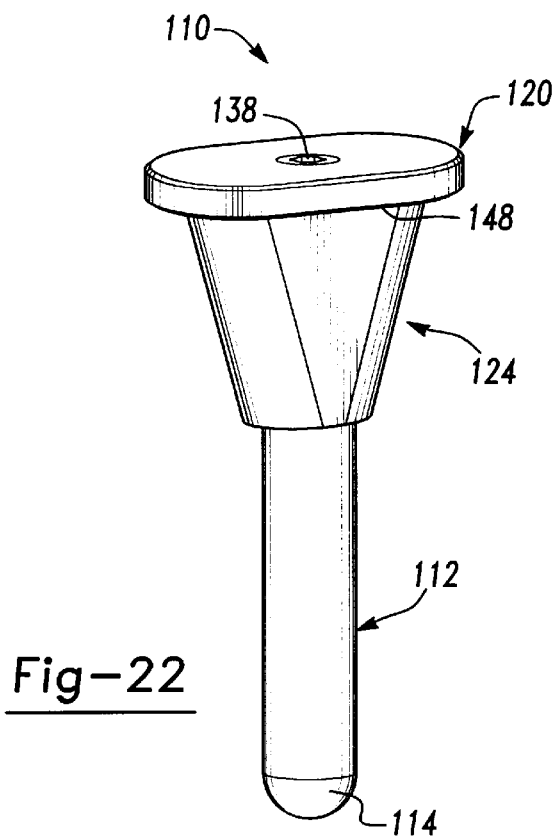
FIG. 22 is a perspective view of the tibial prosthesis of FIG. 19, shown fully assembled with the stem component in its maximally extended position.
Figure 23:
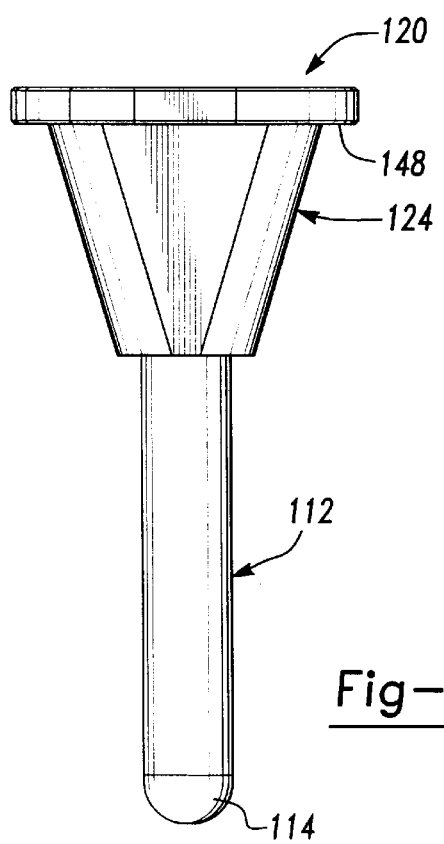
FIG. 23 is a side view of the prosthesis of FIG. 19, shown in an assembled state with the stem in its maximally-extended position and its transition module proximally abutting the distal surface of the tray.
Figure 24:
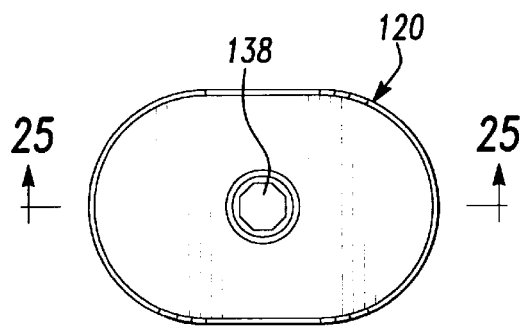
FIG. 24 is an external top view of the tibial prosthesis of FIG. 23.
Figure 25:
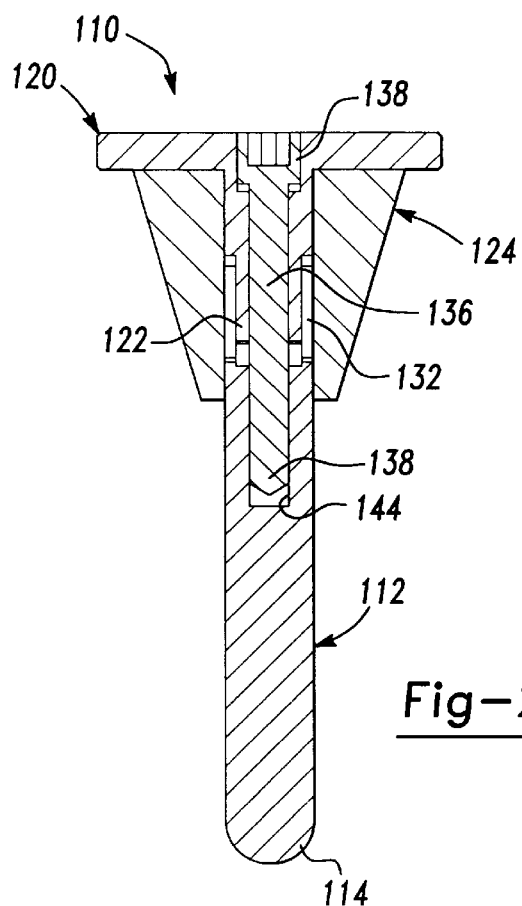
FIG. 25 is a longitudinal sectional view of the tibial prosthesis of FIG. 23, taken along the lines 7—7 of FIG. 24.
Figure 26:
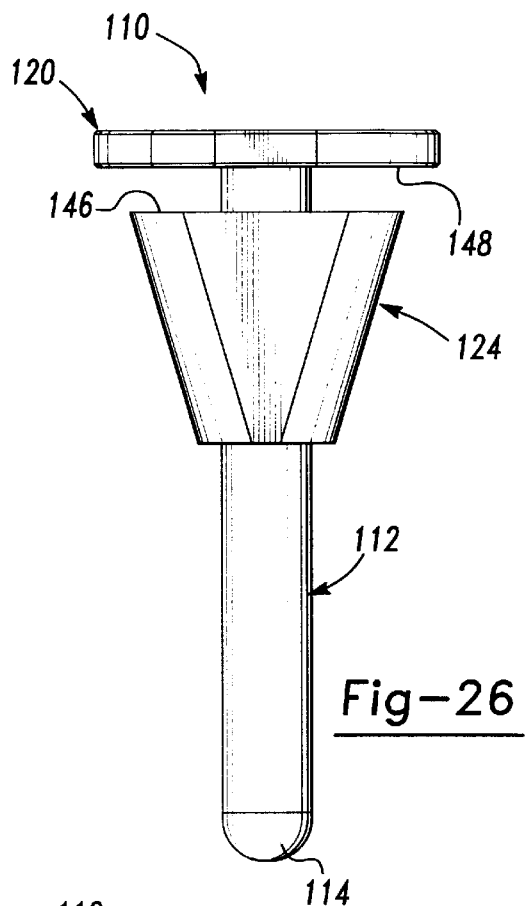
FIG. 26 is a side view of the prosthesis of FIG. 19, shown in, an assembled state with the stem in its minimally-extended position and its transition module spaced from the distal surface of the tray.
Figure 27:
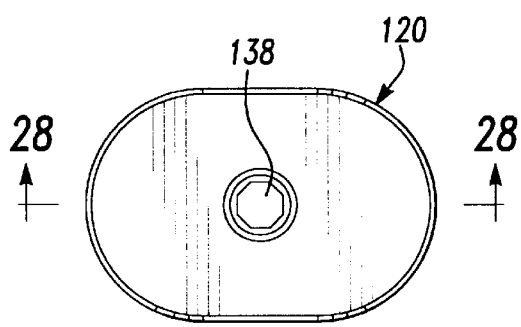
FIG. 27 is an external top view of the tibial prosthesis of FIG. 26.
Figure 28:
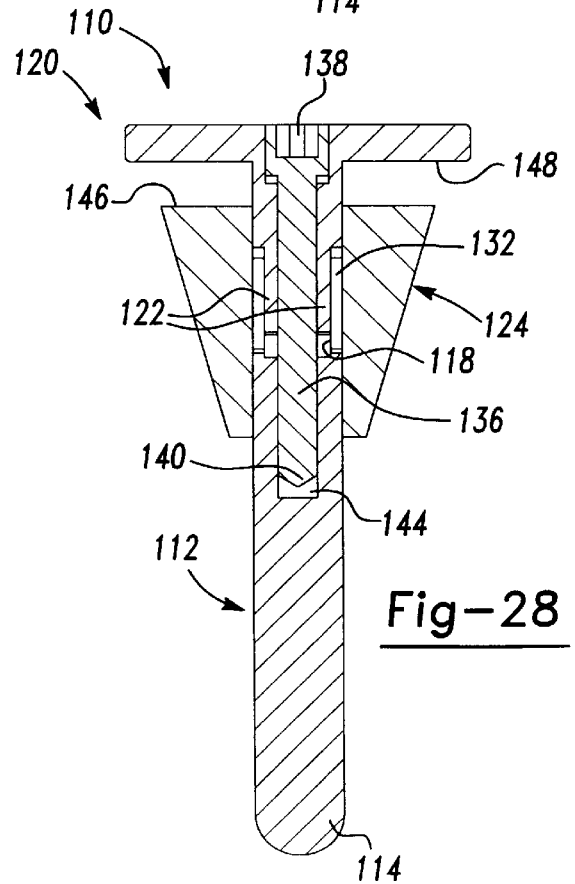
FIG. 28 is a longitudinal sectional view of the tibial prosthesis of FIG. 26, taken along the lines 28—28 of FIG. 27.

Referring to FIGS. 9–11, the mechanism deployed via collet 32 is depicted. FIG. 11 shows the collet 32 expanded radially against the internal surface 30 in the direction of arrows 50, in the manner described above, i. e., by actuation of the locking bolt 34.

In FIG. 12, a hip prosthesis 10 of the present invention is shown having the trochanteric module 24 rotationally adjusted so that the portion of the body 26 which forms a transverse triangular faceted shaped member 52 forms a complex angle with the axis B of the ball post 23 and the axis A of the stem 12.

FIGS. 13–18 show a prosthesis 10 with an alternative juxtaposition of the collet 32 and Morse-tapered bore 18 situated on the neck 20 rather than stem 12, and the tapered post 22 located on the proximal articulating portion of the stem 12. The prosthesis 10, like the embodiment of FIGS. 1–12, may be assembled either with stem 12 in a minimally extended (FIGS. 15–16) or maximally extended (FIGS. 17–18) conformation.

Traditional fixation mechanisms for modular implants typically use Morse tapered connections. The Morse taper is designed to withstand compressive forces and rotational torque, but is not particularly well suited for tension forces and bending moments. It can be shown that bending moments induced on a Morse-tapered connection, where the independent components have dissimilar moments of inertia, can cause surface micro motion at the connection and hence wear, wear debris and eventual failure of the connection. The fully contained radial expansion mechanism described herein, with reference to collet 32, transfers the bending moments induced on the implanted prosthesis 10, due to day to day activities, away from the articulating portions which connect the stem 12 and neck 20 components, toward the strongest portion of the prosthetic joint. Thus the expansion mechanism experiences much less stress than the interface of traditional taper connection modular hip stems.

Independent, infinite rotational variability of the stem 12 to fit the patient advantageously allows for the rotational control of distal bends and coronal slots used commonly on distal stems (not shown) for a better match to the femoral anatomy and reduction in patient pain caused by point stresses against the medullary canal of the femur.

Separate options are available allowing for the cost effective use on the trochanteric module 24 of many popular coatings such as HA, heavy bead blast, or porous coating without the complication of protecting the Morse tapered post.

The surgical procedure for preparing the patient to be implanted with the prosthesis 10 could be chosen from a variety of generally recognized methods and instrumentation, however, an example of a suitable technique is given in the aforementioned U.S. Pat. No. 5,201,882 to Paxson, the entire disclosure of which is expressly incorporated by reference herein and relied upon.

The prosthesis 10 is a modular connection system for use in total joint arthroplasty. Therefore, the rotational and linear extension mechanism of the invention can readily be applied to knee, shoulder and hip joint replacement components each having similar characteristics and functional advantages as it relates to adjustable bone fixation. A tibial prosthesis for use in total knee arthroplasty will be described below.

Referring to FIGS. 19–28, an implantable modular tibial prosthesis 110 is depicted, with an elongated stem 112 having a free distal end 114, configured to be situated within the intramedullary canal of a patient's bone, and an opposite end 116 having preferably a Morse-tapered bore 118. A tibial tray 120 having another articulating portion in the form of a Morse-tapered post 122 matingly engageable with the tapered bore 118 of the stem 112, for attaching the tray 120 and stem 112 together in a selected fixed rotational conformation. A transition module, generally shown at 124, has a body 126 with a linearly-extruded channel 128 having an internal surface 130, through which the articulating tapered bore 118 and post 122 of the stem 112 and tray 120, respectively, are telescopically received. Preferably, the stem 112 is radially-expansible by means of an expanding collet mechanism 132 to pressure lock against the internal surface 130 of the channel 128 in a selected location to arrest the stem 112, tray 120 and transition module 124 together in a fixed axial and rotational relationship as the mating articulating connectors 118, 122 are fully engaged with one another.

A tensioning member, such as the locking bolt 134, operatively connects the stem 112 and tray 120, to urge the tapered bore 118 and post 122 fully together to affix the tray, stem and transition module together in a desired relative conformation.

The locking bolt 134 has an elongated shaft 136 having a driven end 138 and a threaded end 140 which passes through an opening 142 formed in the tray 120 to threadedly engage a tapped aperture 144 in the stem 112.

Although the stem 112 of prosthesis 110 has a Morse-tapered bore 118 and the neck 120 has the complementary Morse-tapered post 122, respectively, these elements could be reversed (not shown), similar to the juxtaposition, described above in FIGS. 1–12 versus FIGS. 13–18, for the hip prosthesis 10. That is, and although not shown in the Drawings, the tray 120 could have the radially expansible collet and tapered bore, rather than having them on the stem, to pressure lock against the internal surface of the channel.

Channel 128 formed in the transition module 124 preferably has a circular cross section, e. g., a cylindrical bore, allowing infinitely variable rotational adjustment of the tray and stem relative to one another, and allowing axial adjustment of the transition module relative to the engaged tray and stem.

While not specifically shown in the Drawings, it will be appreciated from the foregoing discussion that the channel 128 could have a polygonal cross section and the articulating portions could have corresponding shapes which are respectively indexable relative to the channel in a finite selection of rotational alignments.

Referring to FIGS. 19–28, a shoulder 146 is formed on the transition module 124 which abuts a stop 148 formed on the tray 120, limiting the range of axially adjustable telescoping movement of the transition module relative to the tray and stem 112 prior to full engagement of the articulating portions 118, 122 thereof. Prior to tightening of the tapered bore 118 and post 122 together by turning bolt 134, the transition module 124 can be slid in either the proximal direction, to increase the effective length of the stem 112 by abutment of shoulder 146 with stop 148 (FIGS. 22–25), or distally to decrease the stem length (FIGS. 21 and 26–28) leaving the shoulder 146 spaced from stop 148.

A variety of techniques are generally recognized as acceptable for the preparation of the patient's bone to receive the tibial prosthesis of the present invention, these being well known to those skilled in the art.

While I have described certain specific embodiments of the invention for illustrative purposes, various modifications will be apparent to those skilled in the art which do not constitute departures from the spirit and scope of the invention as defined in the appended claims.

I claim:

1. An implantable modular orthopedic prosthesis comprising:
    a first component having an elongated stem with a free end, configured to be situated within the intramedullary canal of a patient's bone, and an opposite end having an articulating portion;
    a second component having another articulating portion matingly engageable with the articulating portion of the first component; and
    a third component having a body with a linearly-extruded channel through which the articulating portions are adjustably received, wherein at least one of the components is radially-expansible to pressure lock against an internal surface of the channel in a selected location and arrest the first, second and third components together in a fixed relative position as the articulating portions are fully engaged with one another.

2. The prosthesis of claim 1 further comprising a tensioning member, operatively connecting the first and second components, to urge the articulating portions together and lock all three components of the prosthesis together in a desired relative configuration.

3. The prosthesis of claim 2 wherein the tensioning member further comprises an elongated shaft having a driven end and a threaded end which passes through an opening formed in the second component to threadedly engage a tapped aperture in the first component.

4. The prosthesis of claim 3 wherein the tensioning member further comprises a locking bolt.

5. The prosthesis of claim 1 wherein the articulating portions of the first and second compoents, respectively, further comprise complementary Morse taper connectors.

6. The prosthesis of claim 5 wherein the articulating portion of the first component has a tapered bore and the articulating portion of the second component has a corresponding tapered post, respectively, for mating engagement with one another.

7. The prosthesis of claim 1 wherein the channel formed in the third component further comprises a cylindrical bore, allowing infinitely variable rotational adjustment of the first and second components relative to one another, and allowing axial adjustment of the engaged first and second components within the cylindrical bore.

8. The prosthesis of claim 1 wherein the first component is radially expansible to pressure lock against the internal surface of the channel.

9. The prosthesis of claim 1 wherein the second component is radially expansible to pressure lock against the internal surface of the channel.

10. The prosthesis of claim 1 further comprising a split collet, which is formed on the radially expansible component and axially constrained within the channel to pressure lock against the internal surface of the channel to affix the three components together.

11. The prosthesis of claim 1 wherein the channel has a polygonal cross section and the articulating portions have corresponding shapes which are respectively indexable relative to the channel in a finite selection of rotational alignments.

12. The prosthesis of claim 1 further comprising a shoulder formed on the third component which abuts a stop formed on the second component, limiting the range of axially adjustable telescoping movement of the third component relative to the first and second components prior to full engagement of the articulating portions thereof.

13. An implantable modular orthopedic prosthesis comprising:
a first component having an elongated stem with a free end, configured to be situated within the intramedullary canal of a patient's bone, and an opposite end having an articulating member comprising a Morse-tapered bore;
a second component having another articulating portion comprising a Morse-tapered post matingly engageable with the Morse-tapered bore formed in the first component, for attaching the first and second components together in a selected fixed rotational conformation;
a third component having a body with a linearly-extruded cylindrical bore through which the articulating members are telescopically received, wherein the second component has a radially-expansible split collet to pressure lock against the internal surface of the cylindrical bore in a selected axial location to arrest the first, second and third components together in a fixed axial and rotational relationship as the mating Morse-tapered members are fully engaged with one another; and
a tensioning member which actuates the collet to radially expand against the internal surface of the bore.

14. An implantable modular hip prosthesis comprising:
an elongated stem with a free end, configured to be situated within the intramedullary canal of a patient's bone, and an opposite end having an articulating portion;
a neck having another articulating portion matingly engageable with the articulating portion of the stem, for attaching the neck and stem together in a selected fixed rotational conformation; and
a trochanteric module having a body with a proximal shoulder and a linearly-extruded channel through which the articulating portions of the neck and stem are telescopically received, wherein at least one of the neck and stem is radially-expansible to pressure lock against the internal surface of the channel in a selected location to arrest the neck, stem and trochanteric module together in a fixed axial and rotational relationship as the mating articulating portions are fully engaged with one another.

15. The prosthesis of claim 14 further comprising a tensioning member, operatively connecting the neck and stem, to urge the articulating portions together to affix the neck, stem and trochanteric module together in a desired relative conformation.

16. The prosthesis of claim 15 wherein the tensioning member further comprises an elongated shaft having a driven end and a threaded end which passes through an opening formed in the neck to threadedly engage the stem.

17. The prosthesis of claim 16 wherein the tensioning member further comprises a locking bolt which threadedly engages a tapped aperture in the stem.

18. The prosthesis of claim 14 wherein the articulating portions of the stem and neck, respectively, further comprise complementary Morse-tapered connecting members.

19. The prosthesis of claim 18 wherein the articulating portion of the stem has a tapered bore and the articulating portion of the neck has a complementary tapered post, respectively.

20. The prosthesis of claim 14 wherein the channel formed in the trochanteric module further comprises a cylindrical bore, allowing infinitely variable rotational adjustment of the neck and stem relative to one another, and allowing axial adjustment of the trochanteric module relative to the engaged first and second components.

21. The prosthesis of claim 14 wherein the stem is radially expansible to pressure lock against the channel.

22. The prosthesis of claim 14 wherein the neck is radially expansible to pressure lock against the internal surface of the channel.

23. The prosthesis of claim 14 further comprising a split collet, which is formed on the radially expansible stem or neck and axially constrained within the channel to pressure lock against the internal surface of the channel and affix the stem, neck and trochanteric module together.

24. The prosthesis of claim 14 wherein the channel has a polygonal cross section and the articulating portions have corresponding shapes which are respectively indexable relative to the channel in a finite selection of rotational alignments.

25. The prosthesis of claim 14 wherein the shoulder formed on the trochanteric module abuts a stop formed on the neck, limiting the range of axially adjustable telescoping movement of the trochanteric module relative to the neck and stem prior to full engagement of the articulating portions thereof.

26. An implantable modular hip prosthesis comprising:
an elongated stem with a free end, configured to be situated within the intramedullary canal of a patient's bone, and an opposite end having an articulating member comprising a Morse-tapered bore;
a neck having another articulating portion comprising a Morse-tapered post matingly engageable with the tapered bore formed in the stem for attaching the neck and stem together in a selected fixed rotational conformation;
a trochanteric module having a body with a linearly-extruded cylindrical bore through which the articulating members are telescopically received, wherein the second component has a radially-expansible split collet to pressure lock against the internal surface of the cylindrical bore in a selected axial location to arrest the first, second and third components together in a fixed axial and rotational relationship as the mating tapered members are fully engaged with one another; and
a tensioning member which actuates the collet to radially expand against the internal surface of the cylindrical bore.

* * * * *